US00PP22096P3

(12) United States Plant Patent
Roose et al.

(10) Patent No.: US PP22,096 P3
(45) Date of Patent: Aug. 30, 2011

(54) MANDARIN TREE NAMED 'DAISYSL'

(50) Latin Name: *Citrus reticulata*
Varietal Denomination: DaisySL

(75) Inventors: Mikeal L. Roose, Riverside, CA (US); Timothy E. Williams, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/456,783

(22) Filed: Jun. 22, 2009

(65) Prior Publication Data

US 2010/0325763 P1 Dec. 23, 2010

(51) Int. Cl.
*A01H 5/00* (2006.01)

(52) U.S. Cl. ..... Plt./202

(58) Field of Classification Search ..... Plt./202
See application file for complete search history.

(56) References Cited

OTHER PUBLICATIONS http://www.citrusaustralia.com.au/aspdev/resources/documents/DaisyB.pdf 2002.Mandarin Variety fact sheet Daisy.*
Froneman et al, Promising seedless citrus selections from the ITSC mutation breeding programme, ITSC Information Bulletin, vol. 17, No. 12, 1996, pp. 12-16.*
http://www.universityofcalifornia.edu/news/article/8234. 2006. Duran UCD Scientists Develop New, Seedless, Mandarin Orange.*
Roose, M. L., et al., "Production of Seedy Fruit by 'DaisySL' Mandarin," Online Article found at http://plantbiology.ucr.edu/faculty/roose.html, Epub Mar. 2010, 4pgs.

* cited by examiner

*Primary Examiner* — Annette Para
(74) *Attorney, Agent, or Firm* — Kilpatrick Townsend & Stockton LLP

(57) ABSTRACT

'DaisySL' is a mid-season maturing diploid mandarin that combines medium-large sized fruit of excellent quality and production with very low seed content even in mixed plantings. It would likely be successful in the mid-season marketing window that currently has very few low-seeded, high quality cultivars.

7 Drawing Sheets

Latin name of the genus and species: The mandarin cultivar of this invention is botanically identified as *Citrus reticulata*.

Variety denomination: The variety denomination is 'DaisySL'.

BACKGROUND OF THE INVENTION

This invention relates to a new and distinctive mandarin cultivar designated 'DaisySL', which was developed at Riverside, Calif. and derived from an irradiated bud of 'Daisy' mandarin. 'Daisy' mandarin was produced in Indio, Calif. in 1963 by J.R. Furr from a conventional hybridization of 2n 'Fortune' x 2n 'Fremont' mandarin. 'Fortune' mandarin was itself produced from a conventional hybridization of 2n 'Clementine' x 2n 'Dancy' mandarin made by J.R. Furr in Indio, Calif. in 1954 and released in 1964. 'Fremont' mandarin was obtained from a conventional hybridization of 2n 'Clementine' mandarin x 2n 'Ponkan' mandarin made by P.C. Reece in Orlando, Fla. in 1948 and later fruited, selected and released by J.R. Furr in Indio, Calif. in 1964.

Irradiation of budwood from registered 'Daisy' trees in Lindcove, Calif. was accomplished in June, 1997 at Riverside. Two hundred buds of 'Daisy' were irradiated as follows: 50 buds were irradiated using 50 Gray units of gamma irradiation from a Cobalt-60 irradiation source; 100 buds were irradiated at 30 Gray units and 50 buds were irradiated at 40 Gray units. Buds from this irradiation were propagated onto various rootstocks in greenhouses at Riverside and Lindcove where they were grown to field-plantable-sized trees. Out of these irradiations, a total of 80 trees were obtained. This low yield of trees is typical because the radiation kills many of the buds. These trees were planted in 1998 at Riverside (28 trees) and Lindcove Research and Extension Center (52 trees). Fruit production and evaluation began in 2001. Only one selection from this irradiated population (propagated on Carrizo citrange rootstock) distinguished itself from the others in having very low seed counts in comparison to the original 'Daisy' cultivar, and with the excellent fruit quality and normal fruit production characteristics of the 'Daisy' parent. Although another tree from the irradiated population had fruit having a lower seed number than the 'Daisy' parent, the fruit had a higher mean seed count and were smaller than the selected variety. After two seasons of fruiting this selection, designated as 'Daisy IR1', was selected for further trials and in January 2003 buds were taken and propagated onto Carrizo and C35 citrange rootstock. Budwood was also sent in April 2003 for evaluation of disease status and elimination of viruses and other pathogens as needed to establish trial plantings. 'DaisySL' was known throughout experimental evaluation as Daisy IR1 (for DAISY IRradiated selection #1). Twenty trees were planted at Riverside in June 2003. Fruit production on these 20 trees commenced in 2006. In June 2004 two trees of 'DaisySL', which had been produced from budwood that had tested and certified as tristeza-free, were sent Lindcove, Calif. where they were planted in the citrus breeding block. In June 2004 seventy-two trees, produced in Lindcove, Calif. were planted (twelve trees each) at six sites, Arvin, Irvine, Lindcove, Oasis, Santa Paula and Woodlake, Calif. All trials were propagated equally on Carrizo and C35 citrange rootstocks. Fruit production of these propagated trees commenced in 2006 (a few trees at each site) and 2007 (all trees at all sites). The properties of 'DaisySL' were found to be true to type and transmissible by asexual reproduction in comparing these plantings with the original 'DaisySL' selection.

BRIEF SUMMARY OF THE INVENTION

'DaisySL' is a mid-season maturing diploid mandarin that combines medium-large sized fruit of excellent quality and production with very low seed content even in mixed plantings. It would likely be successful in the mid-season marketing window that currently has very few low-seeded, high quality cultivars.

BRIEF DESCRIPTION OF THE DRAWINGS

The Figures depict various characteristics of 'DaisySL'.

DETAILED DESCRIPTION OF THE INVENTION

Figure 1:
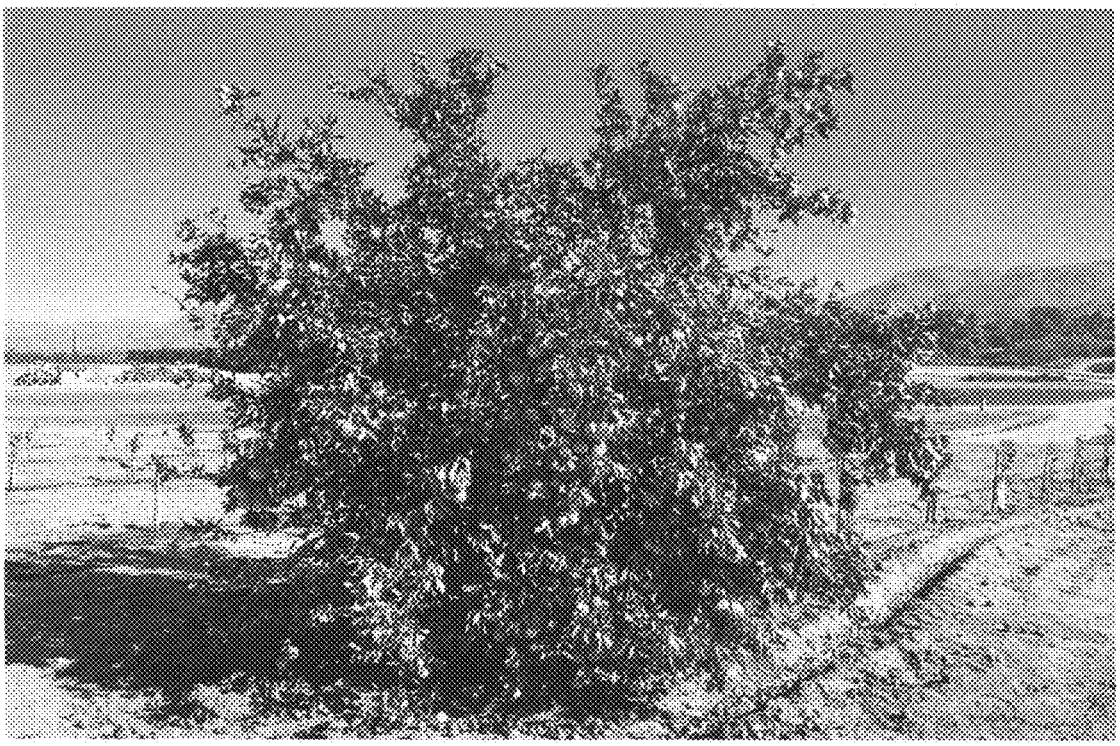
FIG. 1 shows an eight-year-old 'mother' tree of 'DaisySL' on Carrizo citrange rootstock.
Figure 2:
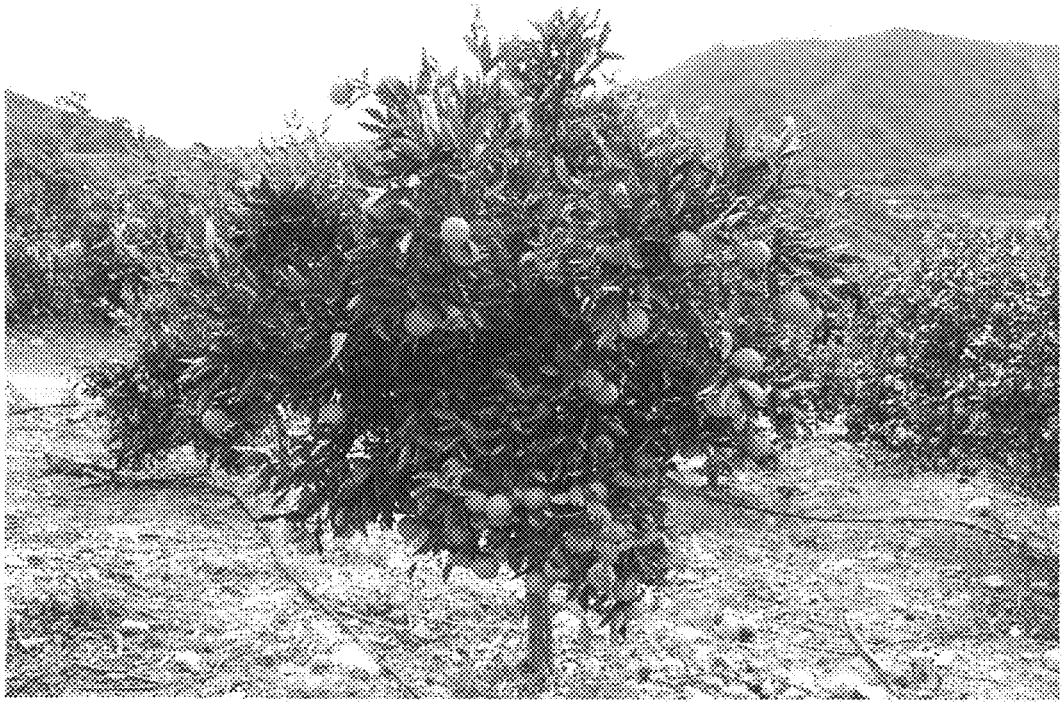
FIG. 2 shows a three-year-old 'DaisySL' tree on Carrizo citrange rootstock at Santa Paula, Calif. (first crop).
Figure 3:
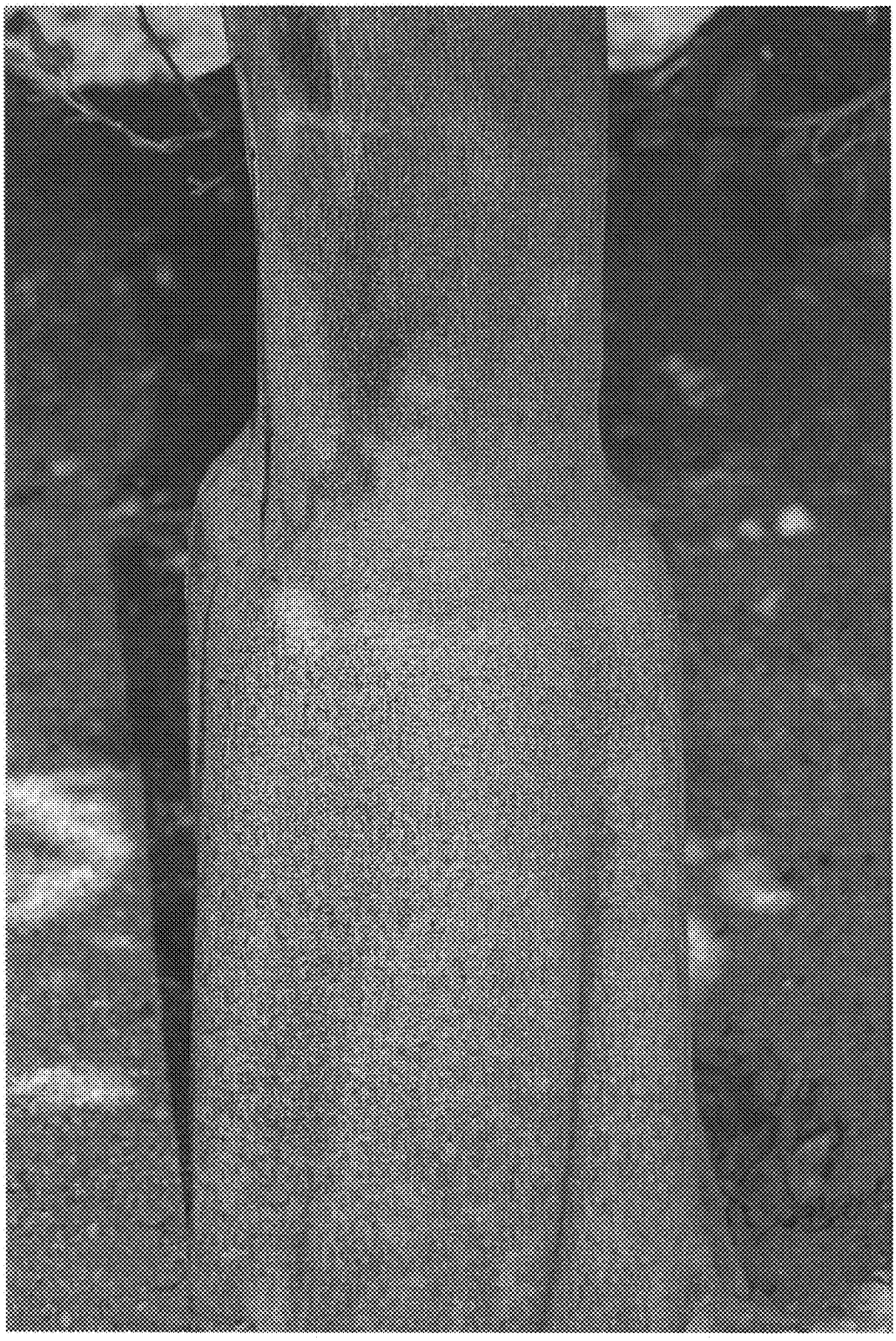
FIG. 3 shows a bud-union of nine-year-old 'DaisySL' on Carrizo citrange rootstock.
Figure 4:
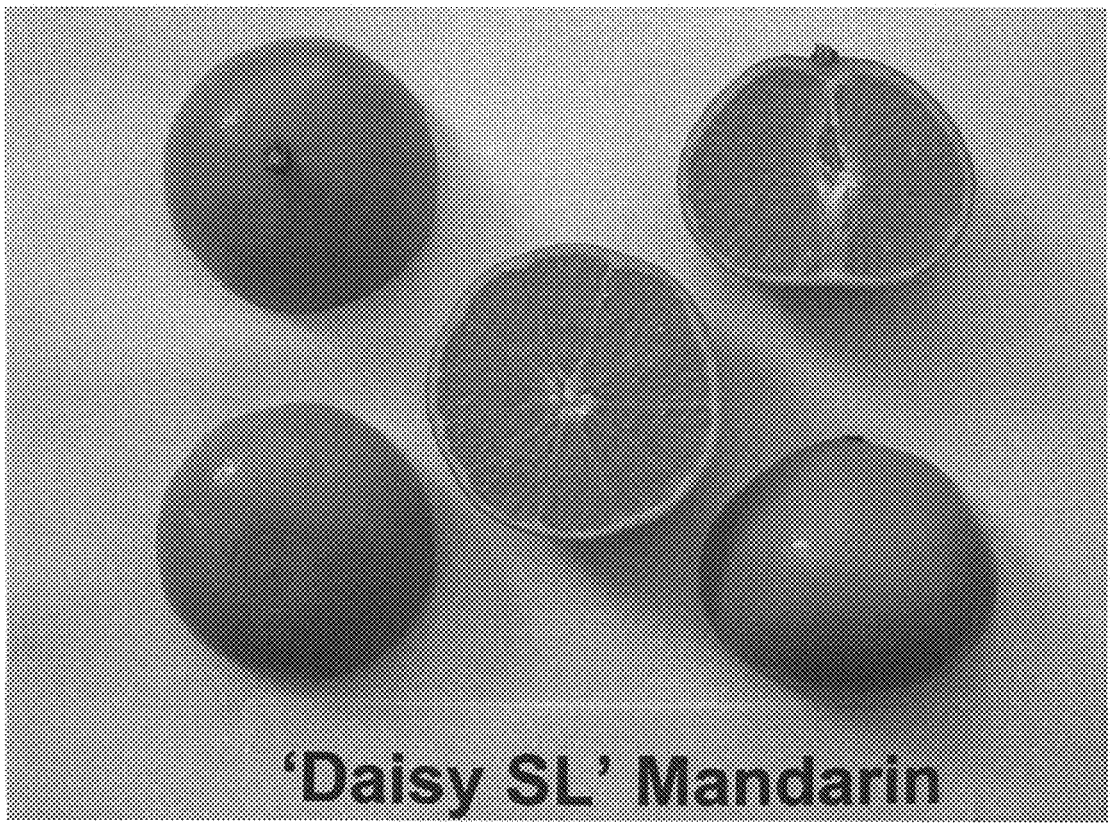
FIG. 4 shows the fruit of 'DaisySL' taken at Riverside in February.
Figure 5:
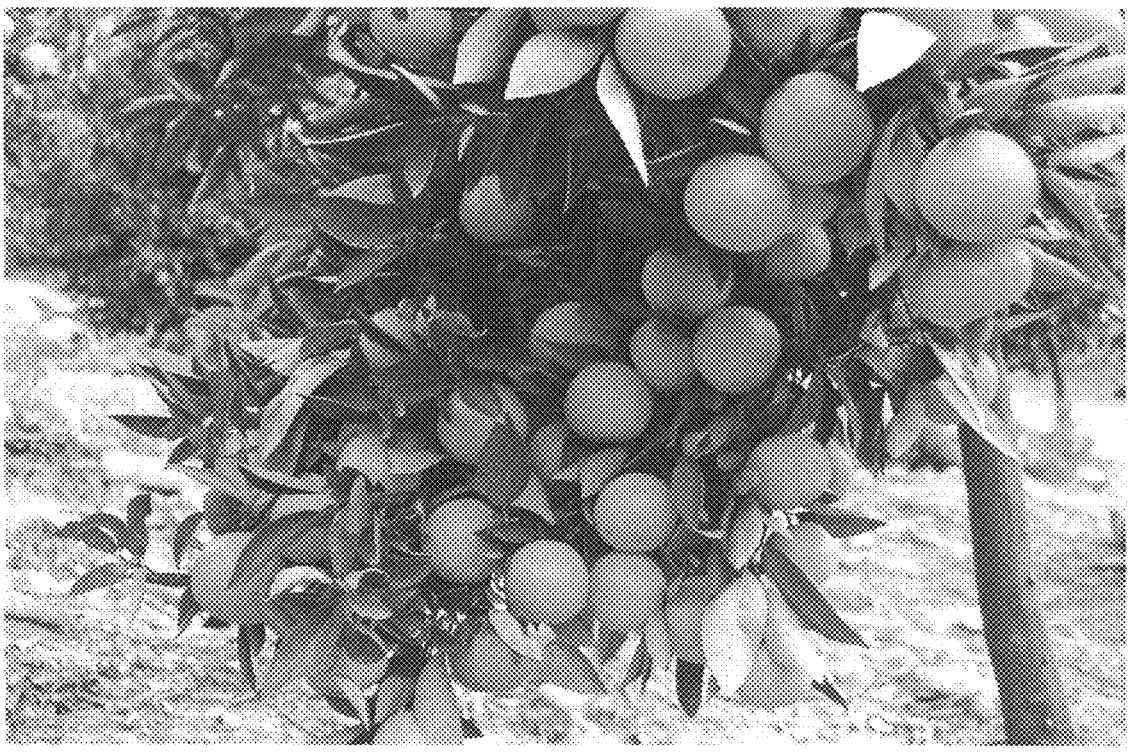
FIG. 5 shows fruit clusters of 'DaisySL' taken at Santa Paula in February.
Figure 6:
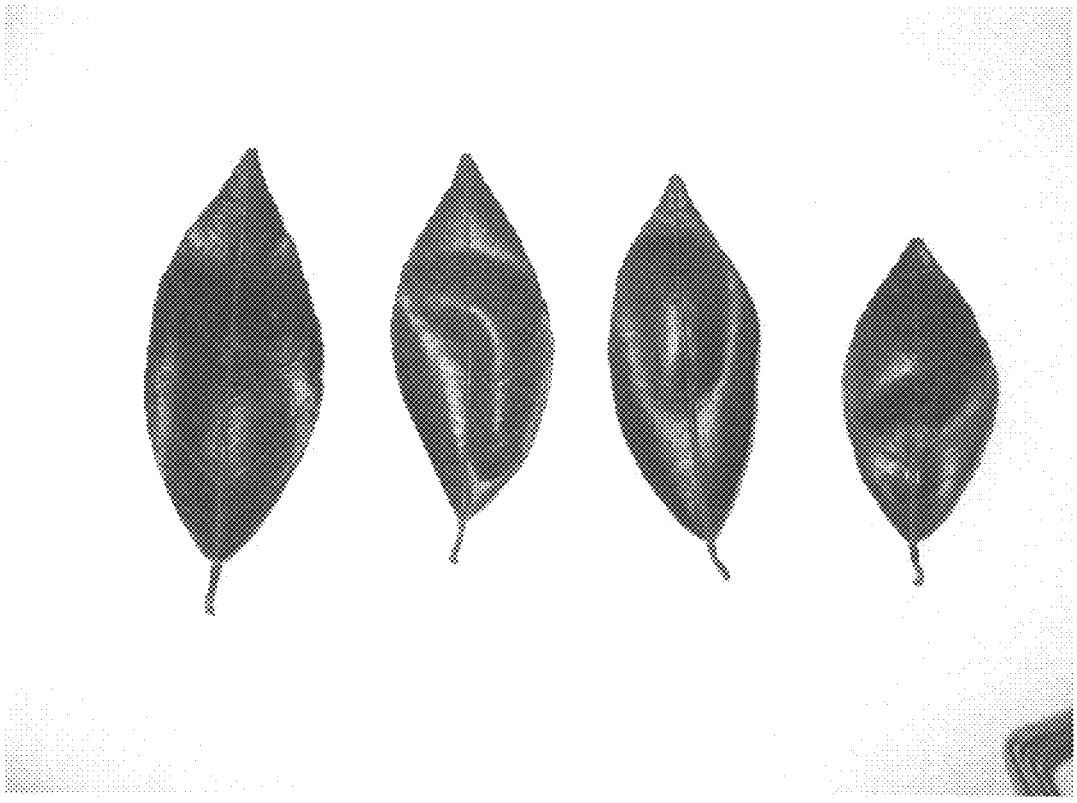
FIG. 6 shows leaves of 'DaisySL'
Figure 7:
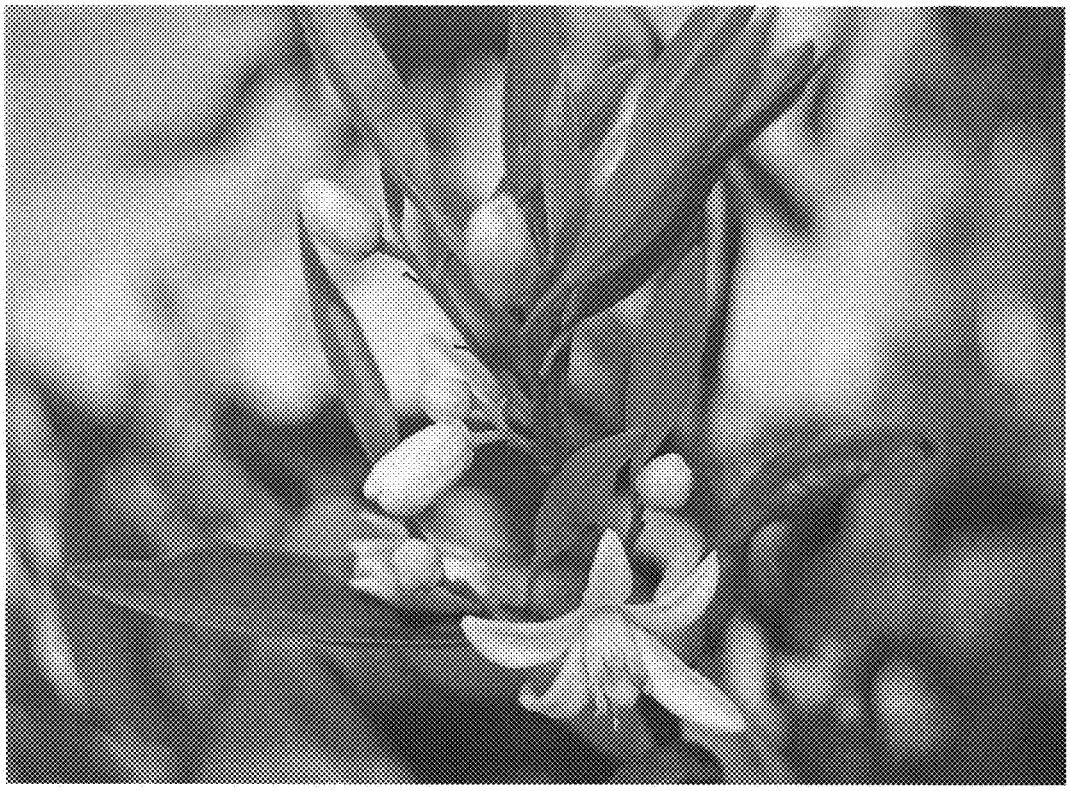
FIG. 7 shows open and closed flowers of 'DaisySL' mandarin

DaisySL' is a mandarin selection developed at the University of California Riverside from an irradiated bud of the diploid mandarin cultivar 'Daisy', a mid-season maturing variety. DaisySL has been asexually reproduced by grafting (budding) using the standard T-bud method generally used to propagate citrus in California. Asexual propagation of the selected tree was first accomplished in January 2003 at the University of California, Riverside to produce 20 trial trees on Carrizo and C-35 rootstocks. 'DaisySL' distinguishes itself by being very low seeded (2.2 seeds/fruit) in all situations of cross-pollination, differing from 'Daisy' which will set from 16-25 seeds/fruit in cross-pollinated situations. In 2010, some trees of 'DaisySL' were found to produce some fruit with seed counts similar to 'Daisy', but only about 1-2% of all fruit were affected. Evaluation of 'DaisySL' mandarin began on the original tree at Riverside in 2001 and has continued annually until the present. In Riverside, Calif. 'DaisySL' fruit matures in winter (early-December). 'DaisySL' holds its fruit quality characteristics through February. Fruit size is moderately large (68 mm) averaging 135 grams per fruit. Fruit are slightly obconate in shape with a very deep orange rind color and an extremely smooth rind texture. Flesh color is very deep orange and finely-textured, fruit are juicy, with a rich, sweet and very distinctive flavor when mature. Fruit are only moderately easy to peel. Tree growth habit is spreading with excellent production commencing in the third year after planting. Alternate bearing can be a problem in trees that are not culturally managed to reduce this tendency.

Cultural practices 'DaisySL' mandarin can be grown according to accepted cultural practices for most mandarin varieties including planting densities of 150-250 trees per acre (375- 625 trees/ha), normal fertilization and pest control practices, and the use of standard rootstocks for mandarins. Pruning may enhance production and health of the tree if applied after the second year of full fruit production. Other rootstocks adapted to more marginal growing conditions of salinity, high pH or very heavy soils may be useful in those conditions.

Comparison with existing mandarins

Mid to late season maturing mandarin cultivars in production include 'Daisy' mandarin (the original cultivar from which 'DaisySL' was derived), 'W. Murcott' (Afourer), 'Fortune' mandarin, Ortanique mandarin, 'Temple' tangor, 'Dancy' mandarin 'Minneola' tangelo, and the mid-season Clementina selections 'Hernandina' and 'Nour'. All of these cultivars will be seedy if grown in the presence of a pollenizer. Some, including the Clementina selections, 'Fortune', 'Ortanique' and 'Page' mandarins will have few seeds if no pollenizer is present. Recently released mid to late season cultivars that are very low-seeded include 'Tango' mandarin, 'Gold Nugget' mandarin, 'TDE2' mandarin hybrid (Shasta Gold(®) 'TDE3' mandarin hybrid (Tahoe Gold®), and 'TDE4' mandarin hybrid (Yosemite Gold®). 'DaisySL' differs from these cultivars in being earlier maturing, having fruit with a smoother rind texture, and a lesser ability to maintain fruit on the tree or in storage for an extended period. Trees of 'DaisySL' show similar alternate bearing characteristics to these cultivars. Additional differences (summarized in Table 6) distinguish it from each of these cultivars.

'DaisySL' mandarin exhibits low seed numbers (<2.5 seeds per fruit) under all conditions of cross-pollination. Additionally, preliminary evaluations indicate that pollen from 'DaisySL' has low germination rates in culture (~10-20%) and appears not likely to cause high seed numbers in other mandarins, specifically 'Tango', 'W. Murcott' and Clementines. A comparison of 'DaisySL' with other low-seeded mid and late-season mandarins is provided in Table 6 below.

'DaisySL' is distinctive and superior in having outstanding flavor, an exceptionally smooth rind, reduced alternate bearing, and larger fruit size preferred in some markets, although it retains the tendency of its parent 'Daisy' for fruit to split at levels approaching 20% in bad years.

Trees, Foliage, and Flowers

Tree size, growth and fruit production characteristics and fruit quality characteristics have been compared in these evaluations to 'Daisy' mandarin from the same field block. Six-year-old 'DaisySL' trees in trials at Riverside, and four-year-old trees at the other six sites have been evaluated for from two to four years of fruiting (see Tables 1 and 2). Tree size and growth characteristics of 'DaisySL' have been consistent with 'Daisy' throughout the evaluations. Growth of both the 'Daisy' and the 'DaisySL' selection has been quite spreading (characterized as 'leggy') in the first several years of growth followed by a tendency to grow into a more spherical, slightly drooping shape in ensuing years. The nine-year-old 'DaisySL' tree at Riverside on Carrizo citrange rootstock is 3.3 m high and 3.7 m wide with a normal upright growth habit yielding a canopy volume of 23.65 $m^3$. In comparison nine-year-old 'Daisy' control trees have averaged 3.2 m tall and 3.6 m wide yielding a canopy volume of 21.7 $m^3$ on Carrizo citrange rootstock. Scion circumference for 'DaisySL' on Carrizo rootstock was 38.5 cm with the rootstock circumference 54.7 cm. Scion circumference for the nine-year old 'Daisy' trees averaged 36.9 cm on Carrizo rootstock and 38.2 cm on C35 rootstock. In the younger multi-location trials five-year-old 'DaisySL' trees on Carrizo rootstock have averaged 2.8 m in height and 3.0 m in diameter with canopy volumes of 8.48 $m^3$ and trees on C35 rootstock averaged 2.9 m in height and 2.7 m in diameter with canopy volumes of 7.48 $m^3$. Leaves of 'DaisySL' are moderately large for a mandarin (86.1 mm in lengthx47.9 mm in width), ovate in shape and concave in cross-section, with an acute apex with weak emargination and a convex base and are dark-green in color (adaxial - RHS Green 139A, abaxial - RHS Green 137C). Petioles are medium in length (9.5 mm) and normally lack wings. The selection lacks thorns. Flowers of 'DaisySL' are hermaphroditic with greenish-white petals and yellowish anthers and are borne in clusters. Pollen viability for 'DaisySL' is moderately low (10-20% germination vs. ~75% germination for 'Daisy'), and pollen production is reduced (30-40% that of 'Daisy') in comparison to 'Daisy'.

TABLE 1

Tree, leaf, flower and seed characteristics (for nine-year-old tree) of 'DaisySL' mandarin

| | | |
|---|---|---|
| 1. | Tree height | 3.7 m |
| 2. | Crown diameter | 3.8 m |
| 3. | Crown shape | Spreading, open |
| 4. | Trunk circumference (on Carrizo rootstock) | 38.5 cm |
| 5. | Bud-union characteristics (citranges) | Slightly benched |
| 6. | Rootstock-scion compatibility | Excellent (with citranges) |
| 7. | Tree vigor | Moderately vigorous |
| 8. | Bark color | RHS Grey-Brown 199B |
| 9. | Leaf shape | Ovate |
| 10. | Leaf cross-section | Concave |
| 11. | Leaf blade length | 86.1 mm |
| 12. | Leaf blade width | 47.9 mm |
| 13. | Leaf apex | Acute with weak emargination |
| 14. | Leaf base | Convex |
| 15. | Leaf margins | Slightly crenate |
| 16. | Leaf abaxial color | RHS Green 137C |
| 17. | Leaf adaxial color | RHS Green 139A |
| 18. | Petiole length | 9.5 mm ± 1.1 |
| 19. | Petiole width | 1.5 mm |
| 20. | Petiole wings | Absent |
| 21. | Petiole color | RHS Green 137C |
| 22. | Thorniness | Not present |
| 23. | Inflorescence type | Clustered |
| 24. | Flowering habit | Flowers once per year |
| 25. | Flower size | 13.0 mm (medium) |
| 26. | Flower structure | Complete |
| 27. | Petal color | RHS White 155C |
| 28. | Anther color | RHS Yellow 13B |
| 29 | Pollen viability* | Low (10-20%) |
| 30. | Trunk texture | Smooth |

(*measured as in-vitro germination)

Fruiting, Fruit and Production Characteristics

Fruit of 'DaisySL' are slightly obconate in shape with no neck. The fruit has a slightly convex basal end (moderately depressed) with a truncate (slightly depressed) distal end, and a distinctive areola and non-persistent style. The fruit is large-sized for a mandarin (classed as Jumbo by State of California standards and size 21 for industry packing standards) averaging 68.0 mm in diameter and 60.1 mm in height with a very smooth, deep orange rind color (RHS Red-Orange N30C) and slightly conspicuous, slightly raised oil glands. The rind is moderately adherent at maturity and relatively thin averaging 3.0 mm in thickness. This rind thinness is implicated in the tendency of 'DaisySL' and its parent 'Daisy' to experience a moderately high level of splitting of fruit, sometimes as high as 20% of the total crop. The fruit interior has a fine flesh texture with 10-11 segments and a semi-solid axis of medium size at maturity. The fruit are juicy, averaging approximately 47% juice and 135 g in weight. Fruit from trees on Carrizo and C35 citrange rootstocks average 11.9-12.8% soluble solids and 1.03-1.28% acid in early December at six trial locations in California increasing to 14.2-15.8% soluble solids and 0.78-0.92% acid in early February. The fruit average 2.2 seeds per fruit in the presence of cross-pollination at all locations. Seeds, when present, are polyembryonic, yellow-white in color (Yellow-White 158B) with greyed-yellow (Greyed-Yellow 160C) colyledons and a greyed-yellow (Greyed-Yellow 163B) inner seed coat.

Full fruit production of 'DaisySL' begins in the third year after planting similar to 'Daisy'. A few fruit will set in the second year after planting but not at commercially acceptable levels. Fruit production on four-year-old trees averaged 27-48 kg at four fruiting trial sites. The original tree at Riverside was similar in fruit production in the fourth year and in years 7, 8 and 9 yielded 77, 32 and 72 kg of fruit respectively indicating that in the earlier years of production the variety has somewhat of a tendency to alternate bear, similar to 'Daisy'.

TABLE 2

Fruit characteristics of 'DaisySL' mandarin at maturity

| | | |
|---|---|---|
| 1. | Fruit shape | Slightly obconate |
| 2. | Fruit diameter | 68.0 mm ± 4.2 |
| 3. | Fruit height | 60.1 mm ± 2.9 |
| 4. | Fruit: shape of basal end | Slightly convex |
| 5. | Fruit: shape of distal end | Truncate (slightly depressed) |
| 6. | Fruit: distal end areola | Present (18 mm ± 1.2 mm in diameter) |
| 7. | Fruit neck | Not present |
| 8. | Style | Not persistent |
| 9. | Rind texture | Smooth |
| 10. | Oil glands | Slightly conspicuous, slightly raised |
| 11. | Rind Color | RHS Orange-Red N30C |
| 12. | Rind thickness | 3.0 mm |
| 13. | Albedo thickness | 1.5 mm |
| 14. | Albedo color | RHS Yellow Orange 23C |
| 15. | Rind adherence | Moderately strong |
| 16. | Rind separation | Very slight |
| 17. | Flesh (pulp) color | RHS Orange-Red N30D |
| 18. | Flesh (pulp) texture | Moderately fine |
| 19. | Number of segments | 10-11 |
| 20. | Axis: structure | Semi-solid |
| 21. | Axis: size | Medium |
| 22. | Navel presence | Not present |
| 23. | # Seeds/fruit (mean) | 2.2 (cross-pollinated conditions) |
| 24. | Seed embryony | Polyembryonic |
| 25. | Seed coat color | RHS Yellow-White 158B |
| 26. | Seed cotyledon color | RHS Greyed-Yellow 160C |
| 27. | Seed inner coat color | RHS Greyed-Yellow 163B |
| 28. | Fruit weight | 135.4 g |
| 29. | % Juice[a] | 46.8% |
| 30. | % Soluble solids (at maturity) | 14.6% |
| 31. | % Acid (at maturity) | 0.98% |
| 32. | Season of maturity | Mid-season (early Dec.-January) |
| 33. | Fruit holding ability on tree past maturity | 1-2 months |
| 34. | Fruit quality after storage (5.6° C., 30 days) | Good |

[a]weight of juice extracted with a reamer as a percentage of fruit weight

TABLE 3

Crop yields for 'DaisySL' and 'Daisy' (control trees) at three trial sites over two years, 2006/2007 and 2007/2008.

| Site | Selection | # Trees | Tree Age 2008 (yrs) | Root-stock | 2006/7 Mean Yield (kg/tree) | 2006/7 Yield Range (kg/tree) | 2007/8 Mean Yield (kg/tree) | 2007/8 Yield Range (kg/tree) |
|---|---|---|---|---|---|---|---|---|
| River-side | 'DaisySL' | 10 | 6.0 | Car-rizo | 32.8 | 24.3-44.9 | 53.8 | 43.3-65.4 |

TABLE 3-continued

Crop yields for 'DaisySL' and 'Daisy' (control trees) at three trial sites over two years, 2006/2007 and 2007/2008.

| Site | Selection | # Trees | Tree Age 2008 (yrs) | Root-stock | 2006/7 Mean Yield (kg/tree) | 2006/7 Yield Range (kg/tree) | 2007/8 Mean Yield (kg/tree) | 2007/8 Yield Range (kg/tree) |
|---|---|---|---|---|---|---|---|---|
| River-side | 'DaisySL' | 10 | 6.0 | C35 | 37.6 | 27.8-48.9 | 54.9 | 47.0-61.4 |
| River-side | 'DaisySL' (mother) | 1 | 9.0 | Car-rizo | 77.1 | 77.1 | 32.1 | 32.1 |
| River-side | 'Daisy' control | 2 | 9.0 | Car-rizo | 70.6 | 67.5-73.6 | 39.4 | 35.2-43.6 |
| Santa Paula | 'DaisySL' | 5 | 4.0 | Car-rizo | 26.4 | 19.8-38.4 | 42.6 | 34.6-55.7 |
| Santa Paula | 'DaisySL' | 5 | 4.0 | C35 | 28.9 | 22.6-34.9 | 44.0 | 37.1-56.4 |
| Santa Paula | 'Daisy' control | 2 | 4.0 | Car-rizo | 26.4 | 24.9-27.9 | 47.9 | 45.1-50.7 |
| Irvine | 'DaisySL' | 9 | 4.0 | Car-rizo | 31.4 | 24.5-39.7 | 45.9 | 38.9-54.8 |
| Irvine | 'DaisySL' | 10 | 4.0 | C35 | 33.6 | 27.4-40.0 | 47.6 | 33.1-57.6 |
| Irvine | 'Daisy' control | 2 | 4.0 | Car-rizo | 28.9 | 27.0-30.8 | 50.1 | 44.0-56.2 |

TABLE 4

Seed counts (average number of seeds per fruit) for 'DaisySL' and 'Daisy' (control trees) at four trial sites over two years, 2006/2007 and 2007/2008.

| Site | Selection | Tree Age (yrs) 2008 | Root-stock | 2006/7 Mean Seeds/Fruit (range) | 2007/8 Mean Seeds/Fruit (range) | % Fruit with 0-2 seeds |
|---|---|---|---|---|---|---|
| Riverside | 'DaisySL' | 6.0 | Carrizo | 2.41 (1.88-3.30) | 1.41 (0.88-2.30) | 81.3 |
| Riverside | 'DaisySL' | 6.0 | C35 | 2.19 (1.50-2.88) | 1.39 (1.02-2.09) | 83.8 |
| Riverside | 'DaisySL' (mother) | 9.0 | Carrizo | 2.26 | 1.86 | 78.9 |
| Riverside | 'Daisy' control | 9.0 | Carrizo | 18.9 | 17.2 | 3.2 |
| Santa Paula | 'DaisySL' | 4.0 | Carrizo | 1.21 (0.78-2.31) | 1.09 (0.69-1.97) | 89.7 |
| Santa Paula | 'DaisySL' | 4.0 | C35 | 1.49 (1.06-2.72) | 1.26 (0.90-2.22) | 86.5 |
| Santa Paula | 'Daisy' control | 4.0 | Carrizo | 15.3 | 14.8 | 5.1 |
| Irvine | 'DaisySL' | 4.0 | Carrizo | 2.16 (1.88-2.76) | 1.61 (1.15-2.32) | 79.9 |
| Irvine | 'DaisySL' | 4.0 | C35 | 2.13 (1.51-2.87) | 1.43 (0.96-2.19) | 81.4 |
| Irvine | 'Daisy' control | 4.0 | Carrizo | 17.4 | 14.9 | 6.1 |
| Lindcove | 'DaisySL' | 4.0 | Carrizo | 2.22 (1.35-3.02) | 1.44 (0.77-2.11) | 86.5 |
| Lindcove | 'DaisySL' | 4.0 | C35 | 2.33 (1.45-2.95) | 1.36 (0.88-1.97) | 88.4 |
| Lindcove | 'Daisy' control | 15 | Carrizo | 17.1 | 16.3 | 3.1 |

TABLE 5

Mean and standard deviation (S.D.) of soluble solids, acid and solids/acid ratio for DaisySL at four trial sites, 2007/8 crop year.

| Site | Date | Soluble Solids % Carrizo | S.D. | Soluble Solids % C35 | S.D. | % Acid Carrizo | S.D. |
|---|---|---|---|---|---|---|---|
| River-side | Dec. 6, 2007 | 12.8 | 0.29 | 12.6 | 0.48 | 1.28 | 0.18 |
| River-side | Jan. 9, 2008 | 14.2 | 0.38 | 14.0 | 0.39 | 1.00 | 0.12 |
| River-side | Feb. 6, 2005 | 15.8 | 0.43 | 15.6 | 0.34 | 0.88 | 0.10 |
| Santa Paula | Dec. 5, 2007 | 11.9 | 0.39 | 12.0 | 0.26 | 0.97 | 0.19 |
| Santa Paula | Jan. 11, 2008 | 13.1 | 0.19 | 13.7 | 0.39 | 0.90 | 0.09 |
| Santa Paula | Feb. 8, 2008 | 14.7 | 0.33 | 14.2 | 0.44 | 0.80 | 0.16 |
| Irvine | Dec. 7, 2007 | 12.1 | 0.66 | 11.9 | 0.49 | 1.03 | 0.14 |
| Irvine | Jan. 7, 2008 | 13.9 | 0.38 | 12.8 | 0.55 | 0.89 | 0.13 |
| Irvine | Feb. 6, 2008 | 15.3 | 0.44 | 13.5 | 0.26 | 0.78 | 0.08 |
| Lind-cove | Dec. 12, 2007 | 12.1 | 0.22 | 12.0 | NA | 1.33 | 0.24 |
| Lind-cove | Jan. 15, 2008 | 13.0 | 0.26 | 13.3 | 0.52 | 1.00 | 0.11 |
| Lind-cove | Feb. 12, 2008 | 15.8 | 0.33 | 15.5 | 0.41 | 0.90 | 0.07 |

| Site | Date | % Acid C35 | S.D. | S/A Ratio Carrizo | S/A Ratio C35 |
|---|---|---|---|---|---|
| River-side | Dec. 6, 2007 | 1.22 | 0.11 | 10.0 | 9.8 |
| River-side | Jan. 9, 2008 | 0.95 | 0.10 | 14.2 | 14.7 |
| River-side | Feb. 6, 2005 | 0.92 | 0.06 | 17.9 | 17.0 |
| Santa Paula | Dec. 5, 2007 | 0.89 | 0.07 | 13.5 | 14.9 |
| Santa Paula | Jan. 11, 2008 | 0.84 | 0.07 | 14.7 | 16.3 |
| Santa Paula | Feb. 8, 2008 | 0.81 | 0.06 | 17.3 | 17.5 |
| Irvine | Dec. 7, 2007 | 1.10 | 0.12 | 11.7 | 10.8 |
| Irvine | Jan. 7, 2008 | 0.90 | 0.14 | 14.5 | 14.2 |
| Irvine | Feb. 6, 2008 | 0.77 | 0.11 | 17.8 | 17.5 |
| Lind-cove | Dec. 12, 2007 | 1.28 | 0.19 | 9.1 | 9.4 |
| Lind-cove | Jan. 15, 2008 | 1.02 | 0.06 | 13.0 | 13.0 |
| Lind-cove | Feb. 12, 2008 | 0.88 | 0.08 | 17.6 | 17.6 |

TABLE 6

Comparison of 'DaisySL' with other late season, low-seeded mandarins. Data for Riverside, California.

| Trait | 'DaisySL' | TDE2 | TDE3 | TDE4 | Gold Nugget | Tango |
|---|---|---|---|---|---|---|
| Maturity | Early December-early January | February | January-February | February | February-March | February-March |

TABLE 6-continued

Comparison of 'DaisySL' with other late season, low-seeded mandarins. Data for Riverside, California.

| Trait | 'DaisySL' | TDE2 | TDE3 | TDE4 | Gold Nugget | Tango |
|---|---|---|---|---|---|---|
| Seeds per fruit | 2.2 | 0.02 | 0.29 | 0.32 | <0.1 | 0.22 |
| RHS rind color | Orange-Red N30C | Orange-Red N3OD | Orange-Red N30C | Orange-Red N30C | Orange 25A | Orange N25A |
| Rind texture | very smooth | slightly pitted | papillate | smooth | bumpy | smooth |
| Fruit weight (g) | 135 | 185 | 134 | 175 | 108 | 90 |
| Fruit height/width | 0.88 | 0.78 | 0.85 | 0.78 | 0.88 | 0.81 |
| Alternate bearing | medium | medium | medium-high | medium-high | high | medium |

Fruit storage trials included storage of washed but not waxed fruit at 5.6° C. for up to 60 days with fruit samples taken every 14 days for analysis. Data indicate that the storage characteristics of 'DaisySL' are fair with some rind deterioration (rind drying) and some significant indication of fungal disease problems in 23% of the fruit. There was no significant deterioration in juice quality or taste over a 30 day storage period in those fruit without fungal pathogens, but with more significant rind deterioration if kept to 60 days. Overall Daisy can only be considered to be fair in storage ability due primarily to the somewhat susceptible nature of the rind to pathogen organisms. Fungicide treatment and waxing might decrease decay and rind deterioration during storage.

No susceptibilities to plant or fruit diseases or to pests beyond those normally associated with citrus species have been observed.

What is claimed is:

1. A new and distinct cultivar of mandarin tree having the characteristics substantially as described and illustrated herein.

* * * * *